United States Patent [19]

Jäppinen et al.

[11] Patent Number: 4,998,431

[45] Date of Patent: Mar. 12, 1991

[54] FIELD USABLE CALIBRATOR FOR HUMIDITY METERS

[75] Inventors: Kalervo A. Jäppinen, Helsinki; Marja-Riitta Hakala; Jouko S. Jalava, both of Vantaa; Ari Lehto, Helsinki, all of Finland

[73] Assignee: Vaisala OX, Helsinki, Finland

[21] Appl. No.: 413,199

[22] Filed: Sep. 27, 1989

[30] Foreign Application Priority Data

Oct. 27, 1988 [FI] Finland ................. 884967

[51] Int. Cl.$^5$ ............................................. G01D 18/00
[52] U.S. Cl. ........................................ 73/1 G; 239/34
[58] Field of Search ............... 73/1 G, 1 R, 29, 335, 73/337.5, 29.01–29.05

[56] References Cited

U.S. PATENT DOCUMENTS

| | | | |
|---|---|---|---|
| 2,239,628 | 4/1941 | Seki | 239/34 |
| 3,209,579 | 10/1965 | Roberts | 73/1 G |
| 3,412,935 | 11/1968 | O'Keeffe | 239/34 |
| 3,618,911 | 11/1971 | Martin | 73/1 G X |
| 3,760,773 | 9/1973 | Christensen | 73/1 G UX |
| 3,776,023 | 12/1973 | Budd et al. | 73/1 G |
| 3,832,882 | 9/1974 | Schuen, Jr. | 73/1 G |
| 3,856,204 | 12/1974 | Chand | 239/34 |
| 4,136,550 | 1/1979 | Pott | 73/1 G |
| 4,139,942 | 8/1983 | Chand | 73/1 G UX |
| 4,849,174 | 7/1989 | Brandt et al. | 239/34 X |

FOREIGN PATENT DOCUMENTS

| | | | |
|---|---|---|---|
| 2247505 | 5/1973 | Fed. Rep. of Germany | 73/1 G |
| 2645736 | 11/1977 | Fed. Rep. of Germany | 73/1 G |
| 13146 | 1/1986 | Japan . | |
| 256249 | 11/1986 | Japan | 73/1 G |
| 928291 | 5/1982 | U.S.S.R. | 73/1 G |
| 1443484 | 7/1976 | United Kingdom | 73/1 G |

OTHER PUBLICATIONS

*Patent Abstracts of Japan;* GRP P465; vol. 10, No. 160 ABS pub. date Jun. 7, 1986 (61-13146).

*Primary Examiner*—Tom Noland

[57] ABSTRACT

Disclosed herein is a humidity calibrator device including a base part sealed by plugs, and a replaceable humidity calibrator cartridge. The cartridge contains saturated vapor, saturated salt solution and salt crystals. The cartridge is sealed with a semipermeable membrane and an air-tight protective peel-off foil. The semipermeable membrane, which seals the part of the humidity calibrator cartridge entering the base part of the apparatus provides a separation of the compartment in the base of the apparatus and liquid containing space of the cartridge, allowing permeation of water vapor and preventing permeation of the liquid.

7 Claims, 2 Drawing Sheets

FIELD USABLE CALIBRATOR FOR HUMIDITY METERS

BACKGROUND OF THE INVENTION

1. Field of the Invention

The present invention relates to a field usable calibrator for humidity meters based on the use of a saturated salt solution.

2. Description of Related Art

The long-term stability of a humidity sensor and its electronic circuitry is influenced by, among other factors, its ambient temperature, humidity and contamination level, which all contribute to the periodical need for meter calibration. Calibration apparatuses capable of generating a known humidity at a known accuracy are available for calibration purposes. In general, the calibration apparatus is a container with a hole, into which the humidity meter is inserted for calibration. The container is air-tight, and an appropriate humidity level is obtained with the help of, for instance, a saturated salt solution, which covers the bottom of the container.

Methods based on the air-tight container and use of a saturated salt solution are relatively effective but during use, the drying and leaking of the salt solution as well as the contamination of humidity meter sensor can generate problems. Aqueous solutions of glycerin and sulfuric acid are also used for the generation of desired humidity, but the use of these substances is awkward due to their toxicity, and the risk of sensor contamination is high. The operation of the humidity meter can also be checked by wrapping the sensor into wetted paper, whereby a relative humidity of approximately 95% is attained after a certain time. The relative humidity level obtained with the help of this method is inaccurate and may lead to contamination or damaging of the sensor.

SUMMARY OF THE INVENTION

The aim of the present invention is to avoid the drawbacks of afore-mentioned methods and to simplify field calibration of humidity meters.

The invention is based on complimenting the base part of the calibrator with an easily replaceable humidity-generating cartridge and inserting the humidity meter into a two-part adapter plug of the apparatus. With the help of the two-part construction of the adapter plug, different sizes of sensors can be attached to the apparatus.

The construction in accordance with the invention provides outstanding benefits.

Several disadvantages of the prior art methods are avoided with the use of the present invention. The replaceable cartridge can be fabricated from transparent plastic allowing for an easy check of liquid volume. The cartridge can be manufactured leak-proof by adhering the semipermeable membrane to the upper part of the cartridge by, e.g., melting. Drying of cartridges during storage can be prevented by a peel-off protective foil. A dry cartridge is easy to replace, and the same base part of the calibrator apparatus can be used with cartridges filled with different sorts of solutions, whereby operating costs are reduced. The sensor can be prevented from touching the humidity calibrator cartridge by an appropriate construction of the apparatus.

In the following, the operating principle and an embodiment of the apparatus in accordance with the invention is exemplified in detail with the help of the attached figures.

DESCRIPTION OF PREFERRED EMBODIMENTS

Figure 1:
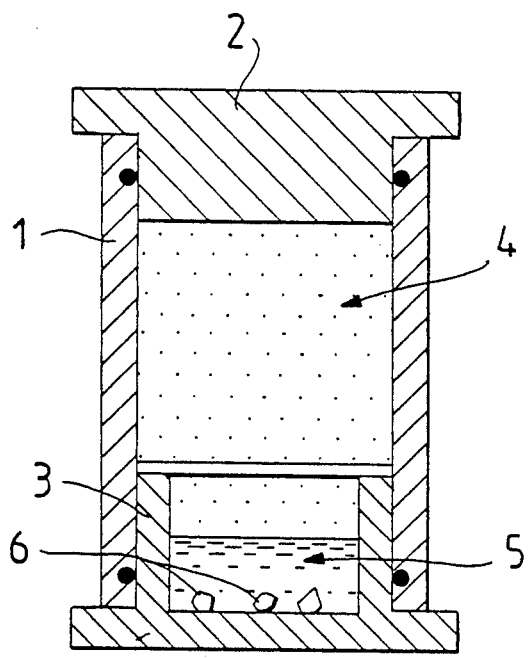
FIG. 1 shows in a longitudinal section the operating principle of an apparatus in accordance with the invention.

The invention is based on the use of a saturated salt solution in the generation of the desired humidity level. The schematic structure of the apparatus is as shown in FIG. 1. The apparatus comprises of two parts, a base part 1 with plug adapters 2 and a humidity calibrator cartridge 3. The humidity calibrator cartridge is filled with saturated salt solution 5, salt crystals 6, and is sealed with a semipermeable membrane 13. The membrane is permeable to water vapor 4 but not to solution 5. In the use of the apparatus, the humidity meter sensor is inserted into the hole of the plug adapter, whereby the sensor provides a hermetic seal for the plug allowing a known humidity level, dependent on the selected salt solution and temperature, to be generated within the apparatus for the calibration of the humidity meter function.

Figure 2:
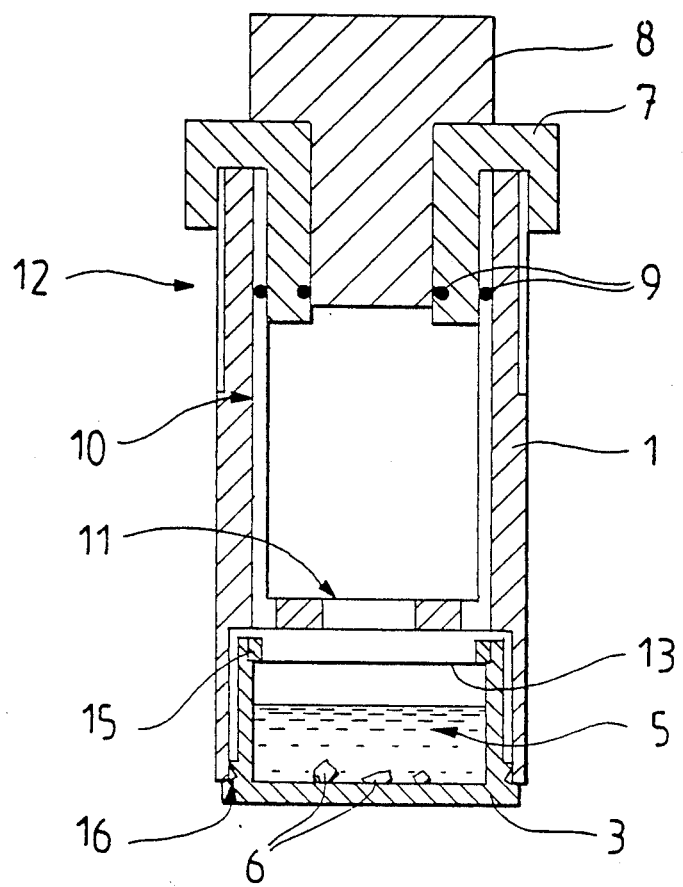
FIG. 2 shows in a longitudinal section the construction of an apparatus in accordance with the invention.
Figure 3:
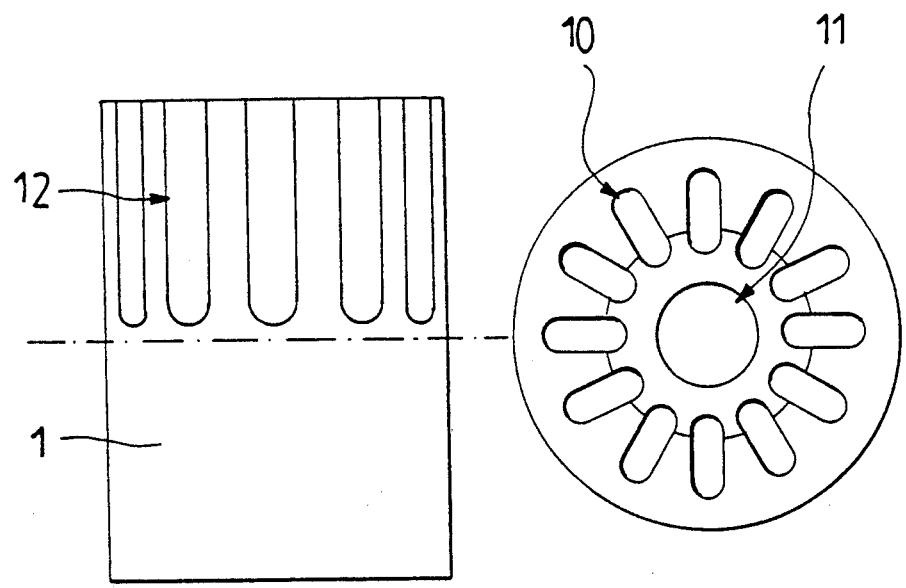
FIG. 3 shows in a side and top view the construction of a base part of the apparatus illustrated in FIG. 2.

FIG. 2 shows an embodiment of the construction of the apparatus. The humidity calibrator cartridge 3 is attached with a quick disconnect union to the base part 1. The two-part plug adapter 7, 8 is inserted to the upper section of the base part 1 and the points are sealed with O-rings 9. The base part 1, plug adapter 7, 8 and humidity calibrator cartridge 3 are manufactured of polycarbonate plastic. The base part 1 is coated on its interior surface by a metallic chromium layer of about 1 $\mu$m thickness in order to avoid the absorption of humidity into the plastic material. The base part 1 has a height of approximately 50 mm and diameter of 35 mm. In order to attain humidity equilibrium in the shortest possible time, the base part 1 is provided with inner grooves 10 and a hole 11. The hole 11 is provided with a collar, which prevents sensor insertion to an excessive depth into the calibrator. For the purpose of more quickly reaching the thermal equilibrium, the outer surface of the base part 1 is profiled with slots 12. The construction of the base part is shown in FIG. 3.

Figure 4:
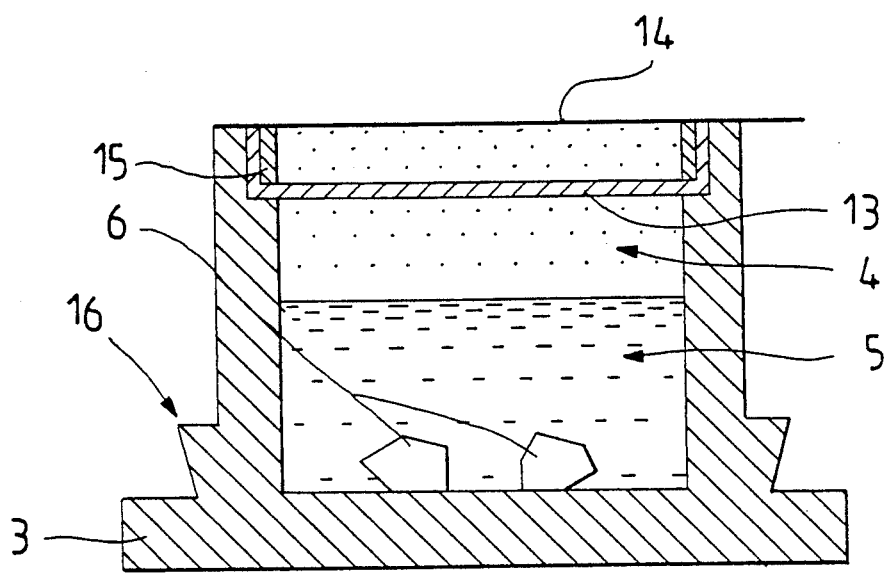
FIG. 4 shows in longitudinal section the construction of a humidity calibrator cartridge of the apparatus illustrated in FIG. 2.

The humidity calibrator cartridge 3 is attached to the lower section of the base part 1 with the help of a quick disconnect union. The construction of cartridge 3 is shown in FIG. 4. The cartridge contains a saturated salt solution 5 and salt crystals 6. A semipermeable membrane 13 and protective foil 14 provide the sealing of the cartridge. Between the protective foil 14 and the solution 5 remains a free space, which is filled with saturated vapor 4. The semipermeable membrane 13 is seamed to the cartridge 3 by a melt point between the seal ring 15 and the upper surface of the cartridge 3 top rim. The melt point ensures the hermeticity of the seam because also the semipermeable membrane is fixed by melting into the seam. The cartridge 8 has a diameter of approximately 30 mm. and volume 5 cm3. The semipermeable membrane 13 is fabricated from polyamide-reinforced polyurethane membrane having approximately 1000 million pores/cm3. The protective foil 14 is an aluminized plastic foil attached to the cartridge 3 by heating. The lower part of the cartridge 3 has collars 16, which provide an air-tight union with the base part 1.

The use of the calibrator apparatus in accordance with the invention is uncomplicated. The first step is to check that the humidity calibrator cartridge 3 contains desired salt solution 5 and that the cartridge 3 is not dry. When required, the cartridge 3 is replaced by a new cartridge. A new cartridge 3 is prepared for use by peeling off the protective foil 14. Depending on the sensor size, the humidity meter sensor is inserted either to a hole in the plug adapter 7 or to the upper end of the base part 1. Hermeticity of the union is provided by O-rings 9. The humidity calibrator cartridge 3 generates vapor 4, which permeates through the semipermeable membrane 13 into the inner space of the base part 1, until the interior of the base part 1 contains a relative humidity level corresponding to the saturated vapor 4 humidity, which is dependent on temperature and selected salt solution. After equilibration of the humidity level, the humidity meter operation can be checked. After calibration, the apparatus is sealed with plugs 7, 8.

Instead of polycarbonate, other alternative materials can be used in the fabrication of the humidity meter calibrator. The material can be selected from several plastic grades, metals or ceramic materials. The base part 3 of the humidity calibrator cartridge must be fabricated from transparent material. Instead of chromium, other metals capable of providing a pore-free metallic coating can be used for coating the base part 1. The base part 1 can be coated either entirely or partly as desired.

What is claimed is:

1. A field usable humidity meter calibrator apparatus based on the use of a saturated salt solution, comprising;
   a hollow base part, which forms a compartment for saturated water vapor and sealable from an upper end with an adapter plug assembly;
   a replaceable humidity calibrator cartridge, which has an inner space containing a liquid and is attachable to a hole provided at a lower end of the base part of the apparatus; and
   a semipermeable membrane, which seals a part of the humidity calibrator cartridge entering the base part of the apparatus and provides a separation of the compartment in the base part of the apparatus and liquid-containing space of the cartridge, allowing the permeation of water vapor and preventing permeation of the liquid.

2. A calibrator as claimed in claim 1, wherein the humidity calibrator cartridge is fabricated from transparent plastic.

3. A calibrator as claimed in claim 1, wherein the semipermeable membrane is a polyamide-reinforced polyurethane membrane.

4. A calibrator as claimed in claim 1, further including an air-tight peel-off foil, which seals the humidity calibrator cartridge.

5. A calibrator as claimed in claim 1, wherein the base part of the apparatus is coated with a pore-free metallic coating at least on its inner side.

6. A calibrator as claimed in claim 1, wherein the base part of the apparatus has an opening with a collar, having an edge which prevents excessive insertion of the humidity meter into the base part.

7. A calibrator as claimed in claim 1, wherein the adapter plug assembly, which seals the upper end of the base part, is comprised of two coaxially mountable plugs.

* * * * *